United States Patent [19]

Kurtz et al.

[11] Patent Number: 5,011,470
[45] Date of Patent: Apr. 30, 1991

[54] COMBINED SURGICAL DRAINAGE AND AUTOTRANSFUSION APPARATUS

[75] Inventors: Robert J. Kurtz, New York; Joseph LiCausi, Port Jefferson Station, both of N.Y.

[73] Assignee: BioResearch, Inc., Farmingdale, N.Y.

[21] Appl. No.: 574,114

[22] Filed: Aug. 29, 1990

[51] Int. Cl.$^5$ .................... A61M 37/00; A61M 1/00
[52] U.S. Cl. .......................................... 604/4; 604/5; 604/9; 604/319; 604/320; 604/321
[58] Field of Search ........................................ 604/4–6, 604/9, 319–21

[56] References Cited

U.S. PATENT DOCUMENTS

| | | | |
|---|---|---|---|
| 4,424,053 | 9/1984 | Kurtz et al. | 604/4 |
| 4,642,088 | 2/1987 | Günter | 604/4 X |
| 4,675,011 | 6/1987 | Kurtz et al. | 604/319 X |
| 4,772,256 | 9/1988 | Lane et al. | 604/4 |
| 4,775,360 | 10/1988 | Lane et al. | 604/4 |
| 4,798,578 | 1/1989 | Ranford | 604/319 X |
| 4,798,578 | 1/1989 | Ranford | 604/4 |
| 4,838,872 | 6/1989 | Sherlock | 604/4 |
| 4,955,877 | 10/1990 | Kurtz et al. | 604/319 X |

Primary Examiner—Alan Cannon
Assistant Examiner—Elizabeth M. Burke
Attorney, Agent, or Firm—Larson and Taylor

[57] ABSTRACT

A combined surgical drainage device and autotransfusion apparatus is provided in which a drainage device having a conventional collection chamber and suction regulating system may be readily converted into use as an autotransfusion system. The drainage apparatus has a fluid retention chamber disposed immediately beneath the inlet and a fluid outlet is provided in the bottom wall of the retention chamber with a spring pressed closure therein so that a nozzle on a collapsible autotransfusion bag may be inserted into the fluid retention chamber. The autotransfusion bag is collapsible and is provided with removable spreader means to maintain the bag in an expanded condition. When suction is applied to the drainage device, the interior of the autotransfusion bag is maintained at the desired suction level. With a tube connected to the inlet tube on the drainge device with the distal end of the tube at a surgical site, blood is drawn through the tube into the fluid retention chamber and this blood passes into the autotransfusion bag. When the bag is filled, it is removed from the drainage device and the spreaders are removed from the bag so that when the blood is reinfused to the patient through the same passageway through which the blood was fed to the autotransfusion device, the bag will collapse without any air passing into the autotransfusion bag.

14 Claims, 3 Drawing Sheets

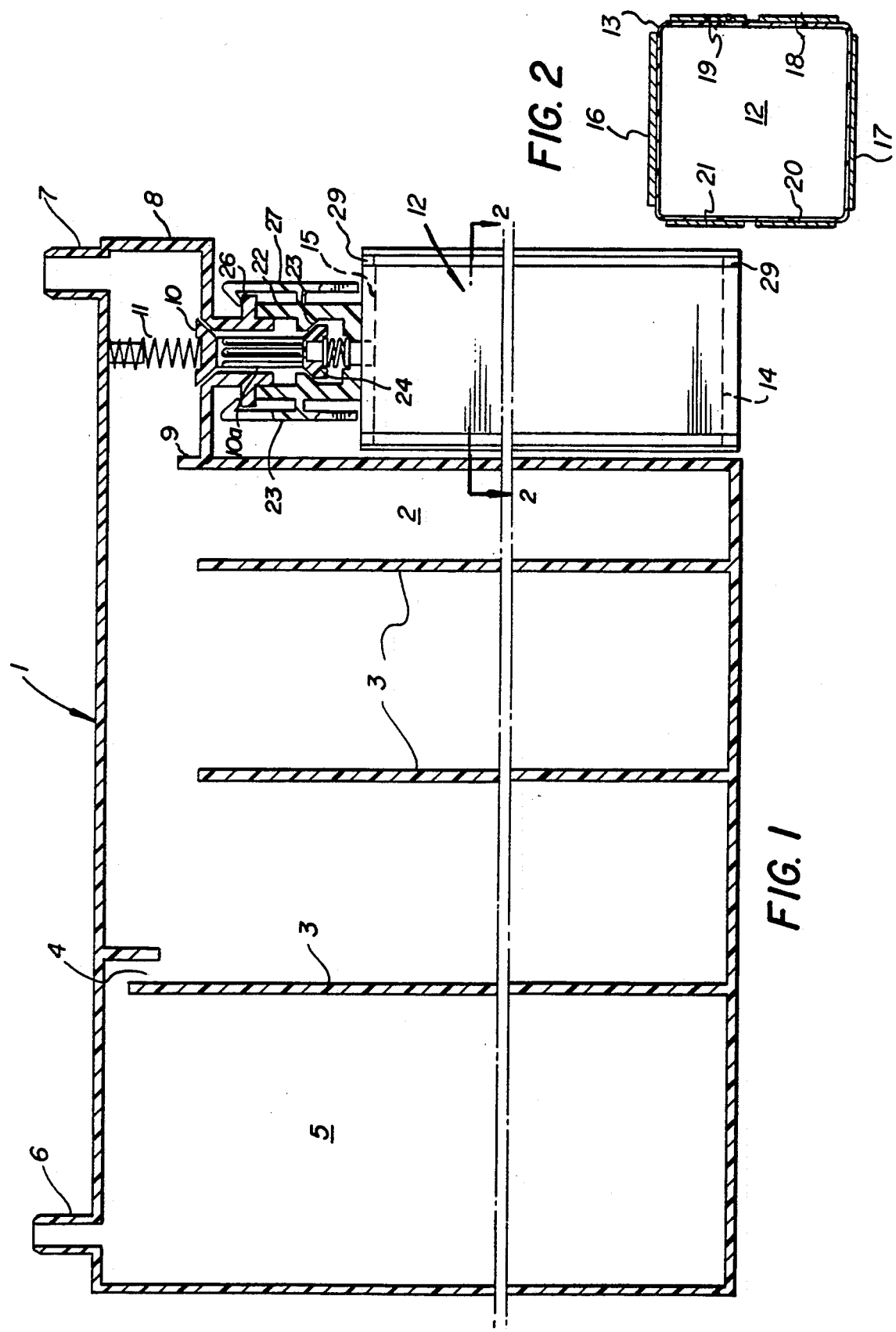

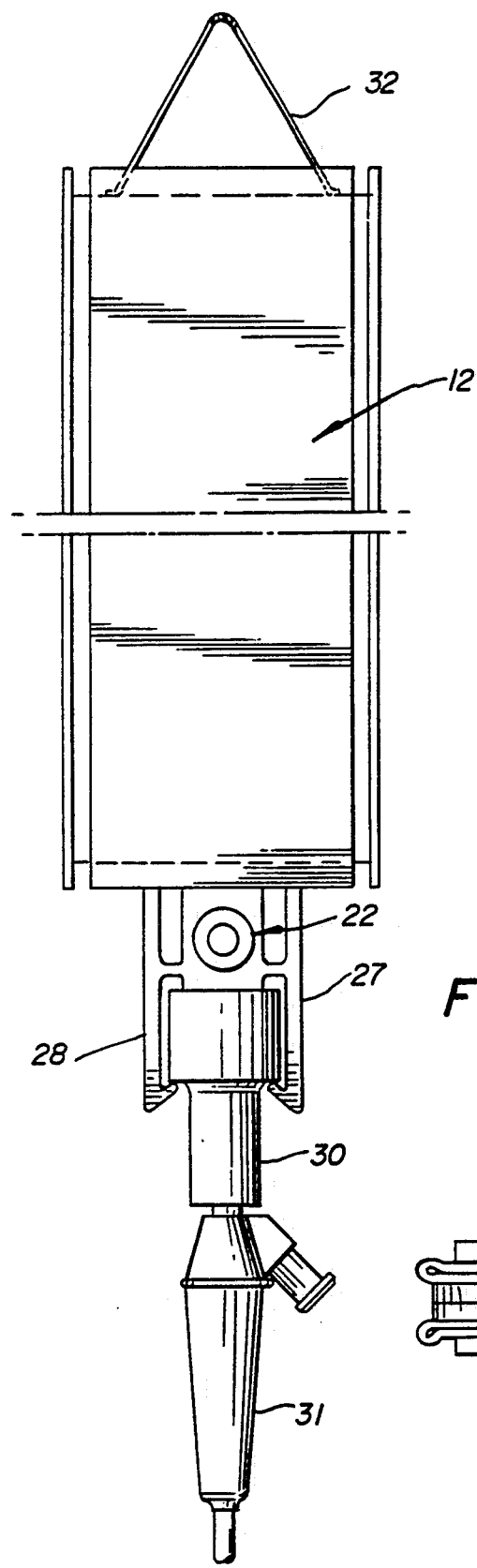
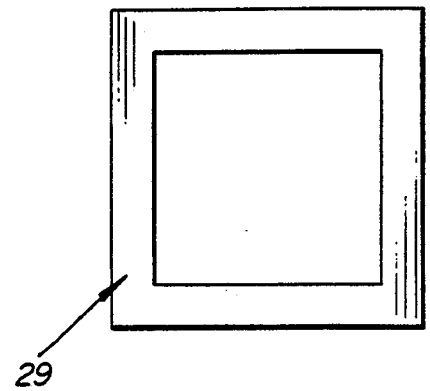
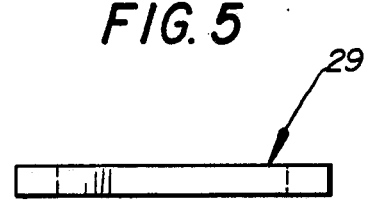
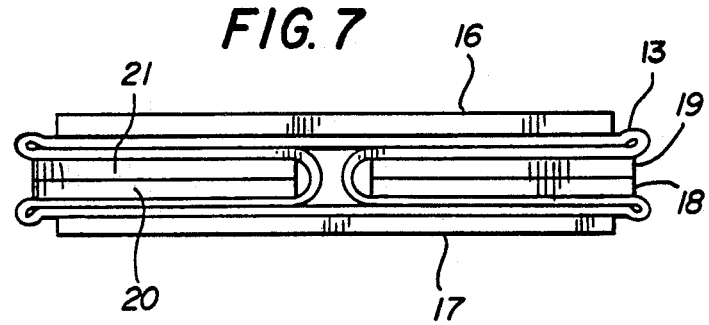

COMBINED SURGICAL DRAINAGE AND AUTOTRANSFUSION APPARATUS

BACKGROUND OF THE INVENTION

The present invention relates to a system which includes a drainage device and autotransfusion bag which permits the apparatus to be used as a conventional drainage device or for the purpose of storing blood from a surgical site and reinfusing the blood into the patient.

There are a number of prior patents disclosing bags or containers which are particularly adapted for use in connection with autotransfusion systems. Generally, these bags are collapsible and provided with means for maintaining bags in an expanded condition when the bag is under suction. For example, the Hauer U.S. Pat. No. 4,443,220 discloses a blood collection bag having pockets around the exterior surface to receive a series of stents mounted on a frame to maintain the bag in an open condition. The bag is then filled with blood while the bag is under suction, the bag is removed from the supporting structure and the patient is then reinfused with the blood with the bag collapsing as the blood is removed therefrom.

The Gunter U.S. Pat. No. 4,642,088 discloses a bag having rigid end wall structures interconnected by a concertina-like structure together with spring means for maintaining the bag in an expanded position. When the bag is filled, the spring is removed to permit the bag to collapse as the blood is being reinfused.

The Sherlock U.S. Pat. No. 4,838,872 discloses a blood collection device including a collapsible autotransfusion bag with pliable walls and stiffener members. A holder for the bag is provided and by applying compressive forces to the sides of the stiffener members, the bag is expanded and forced into the holder to retain the bag in an expanded position while blood from the surgical site is collected within the bag. The autotransfusion device may be connected to a drainage device including a collection chamber suction manometer and outlet to a suction source.

All of the autotransfusion devices in the prior art require multiple ports and are difficult to operate and expensive to produce. There is a need for an inexpensive, simple and easy-to-operate autotransfusion system. The presently disclosed invention overcomes all of the difficulties inherent in using prior art systems.

SUMMARY OF THE INVENTION

According to applicants' invention there is provided a drainage device having a conventional suction regulator and collection chamber with an outlet to a suction source and an inlet which may be connected to a thoracotomy tube or the like. A fluid retention chamber is disposed immediately beneath the inlet to the drainage device and the fluid retention chamber has an opening in the bottom wall which is normally closed by a spring actuated valve. An autotransfusion bag is provided with a single nozzle connector thereon which is adapted to force open the spring valve in the drainage device so as to provide a passageway from the fluid retention chamber in the drainage device to the interior of the autotransfusion bag. The autotransfusion bag is made of a flexible material having rigid panels secured thereto with a spreader means for maintaining the collapsible bag in an expanded position.

When the drainage device is to be used as an autotransfusion system, the autotransfusion bag in an expanded position is connected to the drainage device through the nozzle passageway into the fluid retention chamber. Thus, blood collected in the fluid retention chamber from the surgical site is collected in the autotransfusion bag. The passageway within the nozzle of the autotransfusion bag also serves the function of maintaining the vacuum within the autotransfusion bag by the suction regulator of the drainage device.

When the autotransfusion bag is filled with blood, the bag is removed from the drainage device and a sterile cap is placed over the end of the nozzle until the blood is to be reinfused into the patient.

Upon reinfusion an IV set is inserted through a membrane in the sterile cap and the spreaders which maintain the autotransfusion bag in an expanded condition are removed so that as the blood is reinfused into the patient the autotransfusion bag collapses.

An object of the present invention is to provide a drainage device which is adapted to receive an autotransfusion bag to provide an autotransfusion system for withdrawing blood from a patient's surgical site and reinfusing the blood in the patient.

Another object of the present invention is to provide a collapsible autotransfusion bag having a single passageway which is utilized as both inlet and outlet ports for collecting blood and reinfusing the blood and also for the purpose of maintaining a vacuum within the autotransfusion bag.

Still another object of the present invention is to provide a conventional drainage device with a fluid retention chamber disposed in the passageway between the inlet to the drainage device and the collection chamber with the fluid retention chamber having a removable closure member therein.

Other objects and many of the attendant advantages of the present invention will become more readily apparent on consideration of the following detailed specification in connection with the accompanying drawings wherein:

BRIEF DESCRIPTION OF THE DRAWINGS

FIG. 1 is a cross-sectional view of a drainage device and autotransfusion bag,

FIG. 2 is a cross-sectional view through the autotransfusion bag along the lines 2—2 of FIG. 1, FIG. 4 is a plan view of the spreader for maintaining the bag in an expanded condition, FIG. 5 is a side elevation of the spreader shown in FIG. 3, FIG. 6 is a side elevation of the autotransfusion bag in a position to reinfuse the blood contained in the bag, and FIG. 7 is a cross section through the autotransfusion bag shown in collapsed position.

DESCRIPTION OF THE PREFERRED EMBODIMENT

Figure 3:
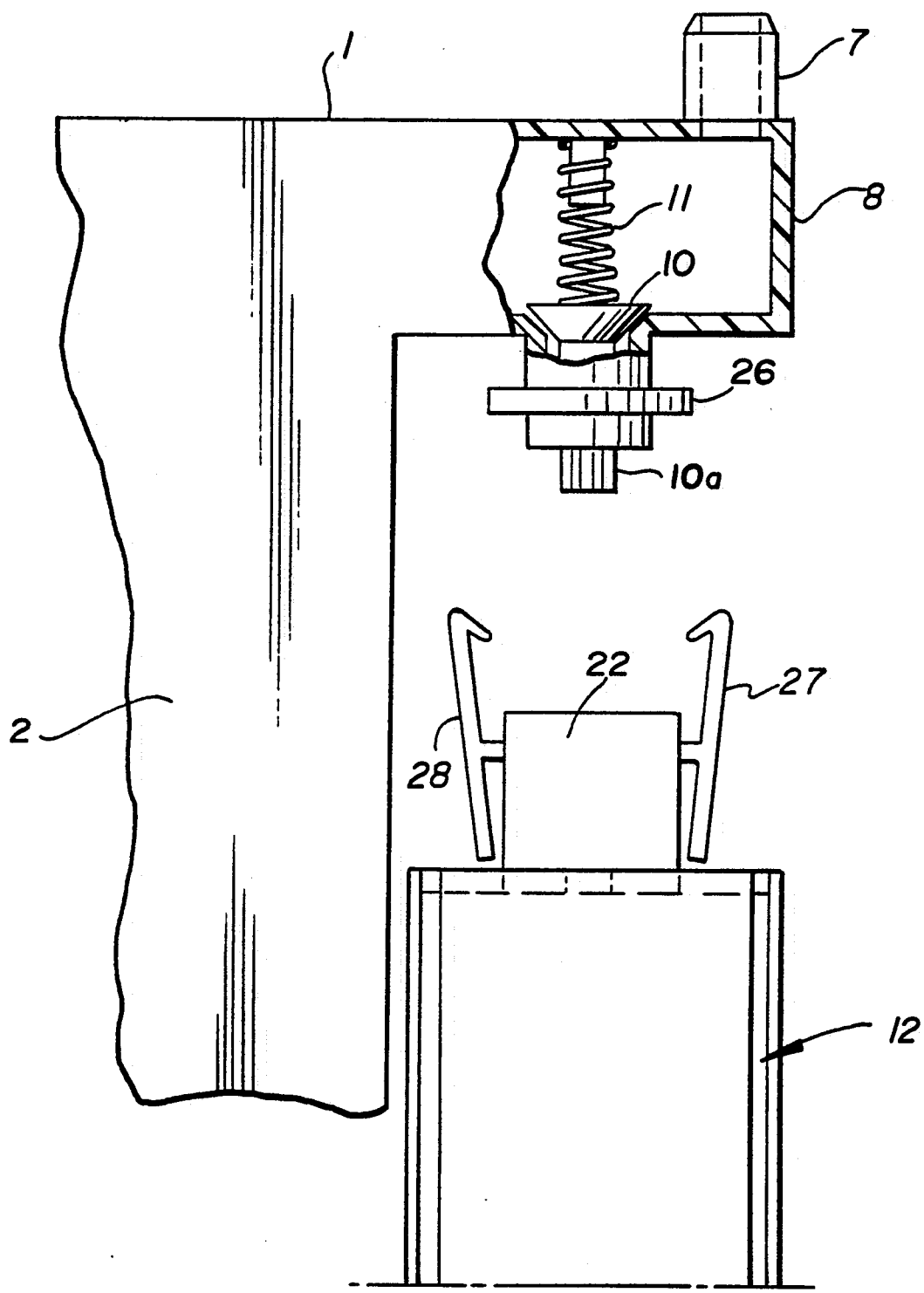
FIG. 3 is a partial cross-sectional view showing the bag removed from the drainage device.

There is shown at 1 in FIG. 1 a drainage device of the type generally used in connection with thoracic surgery. The details of construction of the device are shown generally in U.S. Pat. No. 4,675,011 issued June 23, 1987. The device includes a collection chamber 2 including a plurality of partitions 3 and a passageway 4 to a water seal and suction control chamber 5. The details of construction of the water seal and suction control means are well known in the prior art and shown, for example, in U.S. Pat. No. 4,675,011. There is provided an outlet 6 leading to a suction source and an inlet 7 which is connected with a thoracotomy tube 5 leading to the patient.

The inlet 7 is located at the upper end of a fluid retention chamber 8 formed at the upper end of the drainage device immediately adjacent to the collection chamber 2. As shown in FIG. 1, the fluid retention chamber has a fluid retainer wall 9 which extends partially across the opening between the fluid retention chamber 8 and the collection chamber 2. The bottom wall of the fluid retention chamber has an aperture therein which is normally closed by a closure member 10 which is held in the closed position by means of a spring 11 as shown in FIG. 3. The closure member 10 and spring 11 provide a spring loaded valve which may be opened by insertion of a nozzle or probe externally of the drainage device. The closure member 10 has an elongated fluted cylindrical extension 10a projecting through the opening in bottom wall of the retention chamber.

The drainage device 1 functions conventionally when the spring loaded closure member 10 seals off the port in the fluid retention chamber 8. Liquids and gases from the patient's pleural cavity flow through the thoracotomy tube and inlet 7 into the fluid retention chamber 8. The suction control system maintains the proper level of vacuum within the pleural cavity and any air flow through the inlet 7 passes out through the suction outlet 6. Liquids collect within the fluid retention chamber 8 and when the liquid level overflows the retainer wall 9 the fluids pass into the collection chamber 2.

The fluid retention chamber 8 and spring loaded closure member 10 facilitate the use of the drainage device as an autotransfusion unit in that a nozzle on an autotransfusion bag may be inserted through the opening in the bottom wall of the fluid retention chamber 8 forcing open the closure member 10 against the resistance of spring 11.

The autotransfusion bag 12 is formed of a soft flexible plastic vinyl as shown at FIG. 2. Preferably the bag is formed with four sidewalls, top and bottom walls. As shown in FIG. 1, the bottom wall 14 and top wall 15 are spaced inwardly from the bottom and top edges of the sidewalls. A pair of rigid panels 16 and 17 are bonded to the outer faces of two opposed sidewalls of the autotransfusion bag. A pair of rigid panels 18 and 19 are bonded to one of the other opposing sidewalls and rigid panels 20 and 21 are bonded to the outer face of the other opposed sidewall. Panels 18 and 19 are spaced apart a distance slightly greater than twice the thickness of the panels and panels 20 and 21 are similarly spaced. This spacing permits the autotransfusion bag 12 to collapse with panels 18 and 19 and panels 20 and 21 folding in accordion fashion between the panels 16 and 17 as shown in FIG. 7.

The top wall of the autotransfusion unit 12 has mounted thereon a tubular element 22 having an opening in the bottom wall to provide access to the interior of the autotransfusion bag 12. The interior surface of the tubular element 22 is provided with a circumferential shoulder or valve seat 23 for seating a spring pressed closure member 24. It can be seen in FIG. 1 that, as the autotransfusion bag 12 is moved upwardly towards the bottom wall of the fluid retention chamber 8, the upper surface of closure member 24 engages the lower surface of extension 10a on closure member 10. When the upper end of tubular element 22 engages collar 26 both closure members 24 and 10 are forced open to provide a passageway from fluid retention chamber 8 into the autotransfusion bag 12. There are provided a pair of flexible locking arms 27 and 28 which are integrally formed with the nozzle member 22. The lower ends of the locking arms can be pressed together so that the hook-shaped elements on the upper ends of arms 27 and 28 can pass over the external surface of collar 26 as shown in FIG. 3. The locking arms 27 and 28 may then be released so that the hooks on the ends of the arms engage the upper surface of the collar 26 as shown in FIG. 1.

With the autotransfusion unit in the position shown in FIG. 1, the suction source will maintain the same level of suction in the autotransfusion unit 12 as in the collection chamber 2. The collapsible autotransfusion unit 12 is maintained in an expanded position by means of a spreader frame 29 shown in plan view in FIG. 4. It can be seen that the spreader frame comprises an integrally formed rectangular-shaped member having a central opening which surrounds the tubular member 22 and has the outer surface thereof in engagement with the end portions of panels 16–21. A similar spreader member 29 is also disposed in engagement with the bottom wall 14 of the autotransfusion bag and is in engagement with the inner surfaces of the end portions of panels 16–21. The spreader members serve to resist the collapse of the autotransfusion bag when suction is applied to the bag from the suction source.

With the autotransfusion bag 12 in engagement with the fluid retention chamber 8 as shown in FIG. 1, the apparatus is in a mode to operate as an autotransfusion system. A tube is connected from the inlet 7 to the surgical site so that blood is withdrawn from the surgical site through the inlet opening 7 and into the fluid retention chamber 8, through the opening in the bottom wall of the chamber 8 and into the autotransfusion bag 12. When the bag 12 is filled with blood the lower ends of the locking arms 27 and 28 are pressed together to release engagement of the hook portions of the upper ends of the locking arms 27 and 28 with the collar 26. The autotransfusion may then be removed from engagement with the drainage device 1 and a sterile cap 30 is placed over the tubular 22 and secured in place by means of locking arms 27 and 28 as shown in FIG. 8. The spreader arms 29 are removed from the top and bottom of the bag so as to permit the bag to be collapsed as the blood is withdrawn from the bag. When the blood is to be reinfused into the patient, an IV set 31 is inserted through a membrane at the end of cap 30 and the autotransfusion bag may be suspended from a bracket by a hanger strap 32 mounted on bottom wall 14. As the blood is withdrawn from the bag, the bag will tend to collapse and external pressure on the bag may be applied so that the bag will ultimately assume the totally collapsed position shown in FIG. 7.

The present invention provides an autotransfusion bag which is simple in construction and requires only one port, unlike prior art transfusion bags which require separate ports for the inlet, suction source and outlet. The drainage device to be used with the autotransfusion bag requires minor modifications to adapt it for use both as a conventional chest drainage unit and for autotransfusion purposes.

Obviously many modifications and variations of the present invention are possible in light of the above

What is claimed as new and is desired to be secured by Letters Patent is:

We claim:

1. An autotransfusion bag having a plurality of sidewalls, a top and bottom wall, said sidewalls, top and bottom walls being formed of a flexible material, rigid panels secured to said sidewalls, spreader means engaging said rigid panels for maintaining said sidewalls in spaced relation and single connector means forming a passageway in one end wall of said autotransfusion bag, the passageway in said single connector means providing an air flow path to a suction source, from the autotransfusion bag, a blood flow path from a patient to the autotransfusion bag, and a blood outlet path for reinfusion of blood to said patient from the autotransfusion bag.

2. An autotransfusion bag according to claim 1 wherein said bag has four sidewalls, each of a first pair of opposing sidewalls having a rigid panel covering substantially the entire outer surface each of the first pair of sidewalls, each of a second pair of opposing sidewalls having at least two rigid panels covering substantially the entire outer surface of each of the second pair of sidewalls whereby, when the spreader means is disengaged from the rigid panels, the second pair of sidewalls may be folded between the first pair of sidewalls.

3. An autotransfusion bag according to claim 1 wherein the sidewalls of the bag extend a substantial distance beyond the end wall of the bag and the spreader means comprises a rigid frame fitting within the extended portions of the sidewalls.

4. An autotransfusion bag according to claim 1 wherein said single connector means includes clamping means to attach the autotransfusion bag to a drainage device.

5. An autotransfusion bag according to claim 1 wherein said bag has four sidewalls forming a generally rectangular shaped bag, each sidewall of a first pair of opposing sidewalls having a rigid panel secured to the outer face thereof, the rigid panel covering substantially the entire outer surface of each of the first pair of opposing sidewalls, each sidewall of a second pair of opposed sidewalls having a pair of rigid panels secure thereto, each of said pair of rigid panels having the adjacent edges thereof spaced apart a distance at least equal to twice the thickness of a rigid panel whereby the second pair of sidewalls may be folded between the first pair of sidewalls.

6. An autotransfusion apparatus comprising a drainage device including a collection chamber, a suction regulator for said drainage device, an inlet passageway in said drainage device communicating with said collection chamber, an outlet passageway to a suction source, a fluid retention chamber disposed in the fluid flow path between the inlet passageway and the collection chamber, a fluid outlet in said retention chamber, and removable closure means in said fluid outlet openable by external pressure whereby fluid within said retention chamber may be withdrawn through said fluid outlet into a separable container.

7. An autotransfusion apparatus according to claim 6 wherein said closure means comprises a spring loaded valve.

8. An autotransfusion apparatus according to claim 6 wherein said retention chamber includes a lip whereby when said fluid outlet is closed liquid in the retention chamber overflows into the collection chamber.

9. An autotransfusion device according to claim 6 and further including an autotransfusion bag including nozzle means for opening said closure means to admit fluid from said retention chamber into said bag.

10. An autotransfusion apparatus comprising, in combination, a drainage device including a collection chamber, a suction regulator for said drainage device, an inlet passageway in said drainage device communicating with said collection chamber, an outlet passageway to a suction source, a fluid retention chamber disposed in the fluid flow path between the inlet passageway and the collection chamber, an outlet opening in said fluid retention chamber, a collapsible autotransfusion bag, a single connector means on said autotransfusion bag, said single connector means extending through the outlet opening in said fluid retention chamber, and means operatively associated with said autotransfusion bag for maintaining the autotransfusion bag in an expanded condition, said single connector means having a passageway therein to provide an air flow path from the autotransfusion bag to the suction source and to provide a passageway for blood flow from the fluid retention chamber into the autotransfusion bag.

11. An autotransfusion bag according to claim 10 wherein said bag has four sidewalls, each of a first pair of opposing sidewalls having a rigid panel covering substantially the entire outer surface each of the first pair of sidewalls, each of a second pair of opposing sidewalls having at least two rigid panels covering substantially the entire outer surface of each of the second pair of sidewalls whereby, when the spreader means is disengaged from the rigid panels, the second pair of sidewalls may be folded between the first pair of sidewalls.

12. An autotransfusion bag according to claim 10 wherein the sidewalls of the bag extend a substantial distance beyond the end walls of the bag and the spreader means comprises a rigid frame fitting within the extended portions of the sidewalls.

13. An autotransfusion bag according to claim 10 wherein said single connector means includes clamping means to attach the autotransfusion bag to a drainage device.

14. An autotransfusion bag according to claim 10 wherein said bag has four sidewalls forming a generally rectangular shaped bag, each sidewall of a first pair of opposing sidewalls having a rigid panel secured to the outer face thereof, the rigid panel covering substantially the entire outer surface of each of the first pair of opposing sidewalls, each sidewall of a second pair of opposed sidewalls having a pair of rigid panels secured thereto, each of said pair of rigid panels having the adjacent edges thereof spaced apart a distance at least equal to twice the thickness of a rigid panel whereby the second pair of sidewalls may be folded between the first pair of sidewalls.

* * * * *